United States Patent
Peter et al.

(10) Patent No.: US 7,468,450 B2
(45) Date of Patent: Dec. 23, 2008

(54) PROCESS FOR THE TRANSESTERIFICATION OF FATS AND OILS OF BIOLOGICAL ORIGIN BY MEANS OF ALCOHOLYSIS USING SPECIAL CARBONIC ACID SALTS

(75) Inventors: Siegfried Peter, Lindenweg 3, D-91080 Uttenreuth (DE); Eckhard Weidner, Bochum (DE)

(73) Assignee: Siegfried Peter, Uttenreuth (DE)

( * ) Notice: Subject to any disclaimer, the term of this patent is extended or adjusted under 35 U.S.C. 154(b) by 218 days.

(21) Appl. No.: 11/086,267

(22) Filed: Mar. 22, 2005

(65) Prior Publication Data

US 2006/0058540 A1    Mar. 16, 2006

(30) Foreign Application Priority Data

Sep. 15, 2004    (DE) .................. 10 2004 044 660

(51) Int. Cl.
    *C11C 1/00*    (2006.01)
(52) U.S. Cl. .................. 554/167; 554/169; 554/174
(58) Field of Classification Search .............. 554/167, 554/169, 174
    See application file for complete search history.

(56) References Cited

U.S. PATENT DOCUMENTS

| 2,271,619 | A | 2/1942 | Bradshaw et al. |
| 2,360,844 | A | 10/1944 | Bradshaw et al. |
| 4,668,439 | A | 5/1987 | Billenstein et al. |

FOREIGN PATENT DOCUMENTS

| BR | 8202429 | 11/1983 |
| DE | 1643241 | 2/1973 |
| DE | 3421217 A1 | 9/1985 |
| DE | 19803053 C1 | 4/1999 |
| DE | 10245806 | 4/2004 |
| WO | WO 01/12581 A1 | 2/2001 |
| WO | 0129160 | 4/2001 |
| WO | WO 2004/031119 A1 | 4/2004 |

OTHER PUBLICATIONS

Schuchardt et al., Journal of Molecular Catalysis A: Chemical, "Alkylguanidines as catalyst for the transesterification of rapeseed oil", vol. 99, pp. 65-70, 1995.*
Scuchardt et al., Journal of Molecular Catalysis A: Chemical, "Transesterification of soybean oil catalyzed by alkylguanidines hetrogenized on different substituted polystrenes", vol. 109, pp. 37-44, 1996.*
Schuchardt et al., Journal of Brazilian Chemical Society, vol. 9, No. 3, pp. 199-210, 1998.*
Printout of Rompp Enclyclopedia regarding "Guanidiniumcarbonat"; relevant for providing chemical formula for Guanidine Carbonate and Guanidine; http://www.roempp.com/prod/roempp.php.

* cited by examiner

*Primary Examiner*—Deborah D Carr
(74) *Attorney, Agent, or Firm*—The Webb Law Firm

(57) ABSTRACT

The invention relates to a process for the preparation of fatty acid esters from fats and oils of biological origin by transesterification with monohydric alcohols in the presence of basic catalysts, the catalysts being salts of a basic organic compound and carbonic acid.

14 Claims, No Drawings

PROCESS FOR THE TRANSESTERIFICATION OF FATS AND OILS OF BIOLOGICAL ORIGIN BY MEANS OF ALCOHOLYSIS USING SPECIAL CARBONIC ACID SALTS

FIELD OF THE INVENTION

The invention relates to a process for the preparation of fatty acid esters from fats and oils of biological origin by transesterification with monohydric alcohols in the presence of basic catalysts, the catalysts used being salts of a basic organic compound and carbonic acid.

BACKGROUND OF THE INVENTION

Transesterification reactions are a commercially significant class of industrial organic reactions. In a transesterification reaction an ester is converted to another ester by exchange of the acid groups or by exchange of the alcohol groups. If the transesterification takes place by exchange of the alcohol groups, it is referred to as alcoholysis. In alcoholysis the alcohol to be exchanged is generally added in excess in order to give a high yield of the desired ester. Recently, in connection with the production of diesel fuel from renewable resources, the preparation of alkyl esters, especially methyl esters from vegetable oils (e.g. rapeseed oil, soya bean oil), has acquired considerable relevance.

Transesterification is an equilibrium reaction that is usually initiated simply by mixing the reactants. The reaction proceeds so slowly, however, that for commercial purposes a catalyst is required to accelerate the reaction. Fats and oils of biological origin consist predominantly of glycerides (mono-, di- and triglyceride). In practice the Bradshaw process is often used for the transesterification of fats and oils with methanol (described in U.S. Pat. Nos. 2,271,619 and 2,360,844). The reaction is carried out in an open vessel, which can be made of ordinary carbon steel. In this process the fat or oil, whose acid number should not exceed 1.5, is stirred at the boiling point of the reaction mixture with an excess of 99.7% methanol in the presence of 0.1 to 0.5% of sodium hydroxide. On standing, the glycerol formed separates out at the bottom of the vessel in virtually anhydrous form. After one hour the conversion is usually 98%. The fat or oil must be dry (anhydrous), clean and, in particular, neutral.

If sodium and potassium compounds are used as catalysts in the transesterification of triglycerides with methanol and ethanol, various problems arise. After partial completion of the transesterification reaction, the glycerol produced begins to form a new phase. The sodium and potassium compounds used as catalysts are very readily soluble in the glycerol phase and are accordingly depleted in the reaction mixture. For this reason, and because of the emulsion formed in the course of the reaction, the reaction ultimately progresses only slowly, which is why the reaction is often stopped after about half an hour to separate off the glycerol formed. Fresh catalyst is then added and the reaction is continued for a further half an hour. A conversion of about 98% is obtained in this way. Very fine glycerol droplets still remain suspended in the ester phase after the phase separation. The glycerol and the catalyst partitioned between the two phases must be removed from the ester phase when the reaction has ended. Depending on the subsequent use of the glycerol, it is further necessary also to remove the dissolved catalyst from the glycerol phase. Various suggestions have been made to avoid said problems and simultaneously shorten the reaction time.

Published German patent application DE 34 21 217 A1 describes a process for the preparation of fatty acid esters of short-chain primary and secondary alcohols having 1 to 5 carbon atoms by the transesterification of glycerides, wherein a stream of the gaseous alcohol is passed through the liquid glycerides at temperatures of between 230 and 270° C. A product mixture of glycerol and fatty acid alkyl ester is entrained with this stream out of the reaction zone and is then separated. Alkali is dissolved as catalyst in the liquid glycerides contained in the reaction vessel.

In the process described in German patent DE 198 03 053 C1, triglycerides are reacted with several times the molar amount of alcohol in the presence of suitable catalysts, e.g. zinc soaps, preferably in cocurrent columns at temperatures of 200 to 240° C. and at pressures of up to 90 bar. After the excess alcohol has been separated off, the alkyl ester/glycerol mixtures obtained are separated into the lighter organic phase and the glycerol phase in a separator. This phase separation is followed by a further work-up and purification of the products. The ester phase is washed with water to remove the glycerol residues dissolved in the product. About 40% of the zinc soaps dissolved in the ester is also washed out in the form of zinc hydroxide during this step.

There have also been experiments aimed at replacing the sodium and potassium compounds with basic ammonium compounds as catalysts or reactants. The activity of numerous bases has been studied with regard to their suitability as catalysts for the alcoholysis of fats and oils, examples of said bases being amines such as triethylamine, 1,2,2,6,6-pentamethylpyridine, 2,6-ditert-butylpyridine and 4-dimethylaminopyridine (DMAP); 1,5,7-triazabicyclo(4.4.0)dec-5-ene (TBD), 1,1,3,3-tetramethylguanidine (TMG), 1,2,3-triphenylguanidine, 1,1,2,3,3-pentabutylguanidine (PBG), 1,3-diphenylguanidine and other aminoguanidines and nitroguanidines; and triamino(imino)phosphoranes such as tert-butylamino-2-diethylamino-1,3-perhydro-1,2,3-diazaphorane (BEMP) and tris(dimethylamino)methyliminophosphorane (Me7P). The latter are frequently used in organic synthesis. In one series the catalytic activity of some guanidine compounds, e.g. the amidines DBU and DBN, and the phosphoranes BEMP and Me7P, was compared with that of other bases. The guanidines are the more active catalysts, the activity following their relative basicity. The activity of TBD at a concentration of 3 mol % was similar to that of potassium carbonate at the same concentration.

One advantage offered by guanidines as catalysts in the transesterification of fats and oils is the possibility of binding them to organic polymers. Schuchardt et al. studied the suitability of cellulose, polystyrene/divinylbenzene and polyurethanes as supports. The preparation of heterogeneous catalysts by binding guanidines to various polymers by means of chemical binding forces, and their suitability for catalysing the transesterification of vegetable oils and fats, are described in Brazilian patent BR 8202429 (1984, inventors: U. Schuchardt and O. G. Lopes). The guanidines bound to gelatinous poly(styrene/divinylbenzene) or cellulose showed a slightly reduced activity compared with the catalytic reaction in the homogeneous phase. After prolonged reaction times, however, the same conversion levels were achieved. Although somewhat less active than the analogous homogeneous catalysts, the heterogeneous catalysts could be re-used in a number of consecutive reaction cycles, albeit with a noticeable drop in activity after only 9 reaction cycles. The drop in activity with continuous use was caused by the slow leaching of the anchored base out of the polymer.

Published international patent application WO 2004/031119 describes the use of basic catalysts selected from imino compounds, alkylguanidines, butylamine, quaternary amines and tertiary amines carrying an additional OH group or $NH_2$ group.

In published international patent application WO 01/12581, it is proposed in a first step to deacidify the vegetable oil or fat by reacting the free fatty acids with methanol in the presence of sulfuric acid as catalyst. In a second step, after neutralization, transesterification is carried out using alkali (NaOH, KOH). In the second step, a cosolvent is mixed with the reaction mixture in an amount such that the latter becomes a single phase, thereby considerably increasing the reaction rate. Tetrahydrofuran, methyl tert-butyl ether, pyridine and bis-(dimethylsilyl)trifluoroacetamide are mentioned as suitable cosolvents.

SUMMARY OF THE INVENTION

The object of the present invention is to provide a process for the transesterification of fat and/or oil which is simple to carry out and gives the alkyl ester products in high yields.

This object is achieved according to the invention by a process having the features mentioned in claim 1.

DETAILED DESCRIIPTION OF THE INVENTION

Surprisingly, it has accordingly been found that salts of a basic organic compound and carbonic acid are active catalysts for alcoholysis, especially methanolysis.

Various organic bases, for example guanidine, 1-aminoguanidine, etc., form salts with carbonic acid that crystallize well. In the crystalline state the salts are easy to handle and also stable, storable and inexpensive. The carbonates are insoluble in alcohols and fatty acid esters and sparingly soluble in water. The saturated aqueous solution of guanidine carbonate has a pH of 11 to 11.5. The aqueous solution of free guanidine, on the other hand, gives just as strong an alkaline reaction as lyes. By way of experiment, 2 g of guanidine carbonate were added to a mixture of 100 ml of rapeseed oil and 40 ml of methanol. A stable suspension devoid of unusual features was obtained on stirring. Surprisingly, on heating the mixture, gas bubbles consisting of carbon dioxide formed on reaching temperatures in the region of the boiling point of methanol (60 to 65° C.). It is known that alkali metal carbonates decompose at high temperatures. The higher the basicity of the cation, the higher is the decomposition point. In view of the high basicity of guanidine, the decomposition of guanidine carbonate in a temperature region as low as the boiling point of methanol was surprising.

Sodium hydrogencarbonate already starts to decompose at 100° C. The compound decomposes into sodium carbonate, carbon dioxide and water. However, a decomposition rate sufficient for practical use requires temperatures of 170 to 180° C. Further dissociation of the sodium carbonate starts only when temperatures of about 650° C are exceeded. In comparison, decomposition of the carbonate of the less basic calcium already starts at temperatures of 500° C. The temperature at which a particular alkali metal carbonate dissociates increases with increasing basicity. Ammonium carbonate decomposes into ammonia and carbon dioxide at 58° C. The difference in the basicity of ammonia and guanidine is comparatively very much greater than that between calcium and sodium. The observation that the dissociation of guanidine carbonate in the presence of methanol starts at temperatures as low as approx. 60° C., and that the large difference in basicity between ammonia and guanidine is not reflected in the decomposition point of their carbonates, is all the more surprising.

On refluxing, i.e. evaporation and subsequent condensation of the methanol, the carbon dioxide is transported out of the reaction mixture by the methanol vapour, thereby displacing the dissociation equilibrium until practically only free guanidine is present. Provision could also be made, in principle, to replace the methanol vapour with an inert gas, for example nitrogen, for transporting the carbon dioxide.

In a mixture of ethanol and rapeseed oil, no dissolution of guanidine carbonate or gas formation could be observed even at temperatures above 100° C. Obviously the dissociation of guanidine carbonate at the low temperatures in the region of the boiling point of methanol is to be attributed to a special interaction between methanol and guanidine carbonate. In a mixture of rapeseed oil with a methanol/ethanol mixture, a noticeable reaction could not be observed until the methanol content of the alcohol mixture was at least 30 wt. %, preferably more than 50 wt. % and especially more than 70 wt. %.

If, for example, about 1 wt. % of pulverulent crystalline guanidine carbonate is added to a reaction mixture of rapeseed oil and methanol, a suspension is formed. The guanidine carbonate is insoluble both in the methanol and in the oil. If the suspension is heated, small gas bubbles consisting of carbon dioxide are formed when the temperature reaches about 60° C. With the evolution of the carbon dioxide, free, highly basic guanidine is produced which catalyses the formation of methyl esters. The gas formation becomes more vigorous as the temperature approaches the boiling point of methanol. The free guanidine is soluble in methanol and to a lesser extent also in the oil phase. If the reaction mixture is allowed to reflux, the gas formation subsides markedly after about 10 minutes. After 60 minutes, in one process step, a reaction product of oil and methanol has been formed which corresponds to the European standard for biodiesel fuel, DIN EN 14214. In contrast to the case where alkalis are used as catalysts, it is not necessary to stop the reaction in order to draw off the glycerol formed and bring the reaction to completion with fresh catalyst. Other oils, such as soya bean oil and sunflower oil, yielded analogous results. In summary, the reaction described can be termed a homogeneously catalysed phase transfer reaction.

When the reaction mixture of oil, methanol and guanidine carbonate is refluxed, free guanidine is formed from the guanidine carbonate, said guanidine having a high affinity for $H_2O$ and being capable of binding the $H_2O$ produced in the formation of methyl ester from methanol and free fatty acids. The action in this process is similar to that of the sulfuric acid normally used in the synthesis of ester from alcohol and carboxylic acids. As the guanidine hydrate formed has only a low catalytic activity, this proportion has to be replaced. This can be effected in practice by increasing the amount of guanidine carbonate initially added to the reaction mixture. The free fatty acid content of vegetable oils such as rapeseed oil, soya bean oil, sunflower oil, etc. is about 1 wt. %. An amount of approx. 0.4 to 0.5 wt. % of guanidine carbonate is sufficient to bind the water produced in the reaction of this amount of free fatty acids. In other words, the addition of a total of 1.2 to 1.3 g of guanidine carbonate would be sufficient to convert 100 g of oil to biodiesel fuel within 60 minutes. This obviates the need to remove the free fatty acids from the educt. The degummed oil can thus be converted in a single process step to methyl ester that corresponds to the European standard for biodiesel fuel.

The present invention consequently allows the use of non-deacidified oils with arbitrary free fatty acid contents (e.g. 0.5, 1, 1.5, 2, 2.5, 3, 5, 10 wt. % or higher), which can be efficiently converted to methyl ester by adding appropriately increased amounts of guanidine carbonate (for example an additional 0.2 to 5 wt. %, preferably 0.4 to 0.5 wt. %).

Ethanol is readily obtainable from biotechnological processes and is available in large quantities. However, the direct ethanolysis of triacylglycerides with the addition of guanidine carbonate as catalyst cannot be carried out at low temperatures. Surprisingly, it has now been found that methanol/ethanol mixtures with a minimum methanol content can be reacted at the boiling point of the reaction mixture with the aid of guanidine carbonate as catalyst. With an alcohol mixture made up of equal parts by weight of ethanol and methanol, and rapeseed oil, it was possible, by refluxing for 60 minutes, to produce a product corresponding to the European standard for biodiesel fuel. Free guanidine also catalyses the ethanolysis.

A reaction mixture of 100 ml of rapeseed oil, 40 ml of methanol and 2 g of guanidine carbonate was refluxed for 60 minutes and then cooled. Crystalline particles could no longer be observed in the reaction mixture after about 20 to 30 minutes. The mixture had separated into two phases after cooling. The heavy phase had a volume of 20 ml and the light phase had a volume of 118 ml. After phase separation using a separating funnel, the methanol was separately removed from each phase by distillation, after which the heavy phase had a volume of 10.5 ml and the light phase had a volume of 104 ml. The heavy phase contained 1.6% of methyl esters, 0.1% of monoglycerides and 98.2% of glycerol. The light phase contained 98.6% of methyl esters, 0.5% of monoglycerides, 0.1% of diglycerides, 0.1% of triglycerides, 0.4% of sterols and 0.3% of glycerol. The European standard for biodiesel fuel permits 0.8% of monoglycerides, 0.2% of diglycerides and 0.2% of triglycerides.

When the reaction has ended, the free guanidine acting as catalyst migrates into the heavy phase, in which the bulk of the glycerol produced and excess methanol are dissolved.

The guanidine derivative 1-aminoguanidine also forms a pulverulent crystalline product with carbonic acid. Decomposition of the 1-aminoguanidine hydrogencarbonate is scarcely detectable in the region of the boiling point of methanol. Decomposition of the hydrogencarbonate only proceeds more rapidly at higher temperature. The free 1-aminoguanidine is a catalyst for the methanolysis.

Within the framework of the present invention, the basic organic compounds are strongly basic organic compounds, preferably nitrogen-containing compounds, guanidine and 1-aminoguanidine being preferred. Their carbonic acid salts have the advantage of being stable and easy to handle, simplifying the operation of the process according to the invention.

The alcoholysis is preferably carried out at temperatures ranging from 50 to 120° C. and especially from 65 to 85° C. In one preferred embodiment, the reaction takes place under reflux and/or with vigorous stirring.

The alcoholysis according to the invention is preferably carried out with methanol or a mixture of methanol and another monohydric alcohol. Preferably, the methanol concentration in such a mixture is more than 30 wt. %, especially more than 50 wt. % and preferably more than 70 wt. %. It is preferable to use ethanol as the other monohydric alcohol in a mixture.

In one preferred embodiment, it is possible in a first step to dissolve the guanidine carbonate separately in methanol at elevated temperatures, with the elimination of carbonic acid, and to mix and react this solution with the fat and/or oil to be transesterified. In general, the catalytic activity of free guanidine is noticeably higher than that of guanidine derivatives.

In one preferred embodiment, the molar ratio of methanol to fat and/or oil used is at least 2.3 to 1, preferably 3 to 1 and especially 6 to 1 or higher.

Suitable fats and/or oils are vegetable oils such as rapeseed oil, palm oil or soya bean oil, as well as fish oil, lard, etc. Preferably, the fats/oils contain a proportion of not more than 0.2% of free fatty acids in the starting material. This can be achieved by degumming and deacidifying the starting oils. However, within the framework of the present process, the fats and/or oils can also be used without prior deacidification, as shown in Example 7 below. In another preferred embodiment, untreated oil containing about 1 wt. % to 2 wt. % of free fatty acids is treated with additional guanidine carbonate to bind the water produced in the reaction of the free fatty acids.

Some Examples are now given to illustrate the invention further.

EXAMPLE 1

A mixture of 100 ml (92 g) of rapeseed oil, 42 ml (33 g) of methanol and 0.7 g of guanidine carbonate was stirred under reflux for 60 minutes. After the reaction had been stopped and the reaction mixture cooled, two liquid phases formed. The upper, light phase had a volume of 116 ml and the heavy phase had a volume of 24 ml. By distillation of the methanol under a water-jet vacuum, the volume of the heavy phase was reduced to 7 ml of a liquid having the following composition: 98.2% of glycerol, 1.6% of methyl esters and 0.1% of monoglycerides. The glycerol formed contains the bulk of the guanidine added and is therefore strongly alkaline. After distillation of the methanol under a water-jet vacuum, the light phase had a volume of 106 ml. Apart from glycerol (0.3%), the product contained 98.6% of methyl esters, 0.7% of monoglycerides, 0.2% of diglycerides and 0.5% of sterols (unsaponifiable material).

EXAMPLE 2

A mixture of 100 ml (92 g) of rapeseed oil, 40 ml (31 g) of methanol and 1 g of guanidine carbonate was stirred under reflux for 30 minutes. After the reaction had been stopped and the reaction mixture cooled, two liquid phases formed. The light phase had a volume of 118 ml and the heavy phase had a volume of 22 ml. By distillation of the methanol under a water-jet vacuum, the volume of the heavy phase was reduced to 8.5 ml of a liquid having the following composition: 97.3% of glycerol, 2.4% of methyl esters and 0.1% of monoglycerides. The glycerol formed is strongly alkaline. After distillation of the methanol under a water-jet vacuum, the light phase had a volume of 105 ml. The product contained 98.5% of methyl esters, 0.5% of monoglycerides, 0.1% of diglycerides, 0.1% of triglycerides, 0.4% of sterols (unsaponifiable material) and 0.4% of glycerol.

EXAMPLE 3

A mixture of 100 ml of rapeseed oil, 40 ml of methanol and 0.5 g of guanidine carbonate was stirred under reflux for 60 minutes. After the reaction had been stopped and the reaction mixture cooled, two liquid phases were formed. The light phase had a volume of 116 ml and the heavy phase had a volume of 21.5 ml. By distillation of the methanol under a water-jet vacuum, the volume of the heavy phase was reduced to 8 ml having the following composition: 98.7% of glycerol, 1.2% of methyl esters and 0.1% of monoglycerides. The glycerol formed is strongly alkaline. After distillation of the methanol under a water-jet vacuum, the light phase had a volume of 107 ml. The product contained 98.3% of methyl esters, 0.6% of monoglycerides, 0.2% of diglycerides, 0.1% of triglycerides, 0.4% of sterols (unsaponifiable material) and 0.4% of glycerol.

EXAMPLE 4

A mixture of 100 ml of rapeseed oil, 40 ml of methanol and 1 g of 1-aminoguanidine hydrogencarbonate was stirred under vigorous reflux for 60 minutes (the boiling point was therefore about 0.5 to 1° C. higher than in Examples 1 to 3). After the reaction had been stopped and the reaction mixture cooled, two liquid phases were formed. The light phase had a volume of 64 ml and the heavy phase had a volume of 76 ml. After distillation of the methanol under a water-jet vacuum, the light phase had a volume of 50 ml. The product contained 36.7% of methyl esters, 4.8% of monoglycerides, 27.8% of diglycerides, 29.5% of triglycerides, 0.7% of sterols and 0.5% of glycerol.

EXAMPLE 5

100 ml of rapeseed oil, 20 ml of ethanol, 20 ml of methanol and 1 g of pulverulent crystalline guanidine carbonate were placed in a vessel and stirred under reflux for 60 minutes. The reaction mixture was then cooled to ambient temperature. Two phases were formed. The heavy phase had a volume of approx. 16 ml and the light phase had a volume of approx. 123 ml. Apart from solvent, the heavy phase contained 7.6% of esters and 92.4% of glycerol. Apart from excess alcohols, the light phase contained 98.7% of esters, 0.3% of monoglycerides, 0.2% of diglycerides, 0.1% of triglycerides, 0.4% of sterols and 0.3% of glycerol.

EXAMPLE 6

100 ml of soya bean oil, 40 ml of methanol and 1 g of guanidine carbonate were stirred under reflux for 60 minutes. After the reaction had been stopped and the reaction mixture cooled, two liquid phases were formed. The light phase had a volume of 116 ml and the heavy phase had a volume of 21 ml. After distillation of the excess methanol under a water-jet vacuum, the light phase had a volume of 106 ml. The product contained 99.0% of methyl esters, 0.7% of monoglycerides and 0.3% of sterols and tocopherols. By distillation under a water-jet vacuum, the volume of the heavy phase was reduced to 7.5 ml. The composition of the heavy phase after concentration by evaporation was 98.0% of glycerol, 1.9% of methyl esters and 0.1% of monoglycerides.

EXAMPLE 7

100 ml of palm oil (containing about 1.5% of free fatty acids), 40 ml of methanol and 1 g of pulverulent crystalline guanidine carbonate were placed in a vessel and stirred under reflux for 60 minutes. After the reaction had been stopped and the reaction mixture cooled to 30° C., two liquid phases formed. The heavy phase had a volume of 23.5 ml and the light phase had a volume of 115 ml. Apart from solvent, the heavy phase contained 96.6% of glycerol, 1.6% of methyl esters, 0.6% of monoglycerides, 0.2% of diglycerides and 0.9% of free fatty acids. Apart from solvent, the light phase contained 94.8% of methyl esters, 1.3% of monoglycerides, 1.5% of diglycerides, 0.7% of triglycerides, 1.1% of free fatty acids and 0.6% of glycerol.

The invention claimed is:

1. A method for the transesterification of fat and/or oil of biological origin by means of an alcoholysis reaction, comprising:
    placing the fat and/or oil of biological origin to be transesterified in a vessel; and
    adding methanol and a catalyst, the catalyst being guanidine carbonate and the alcoholysis being carried out at temperatures ranging from 50° C. to 120° C.

2. A method for the transesterification of fat and/or oil of biological origin by means of an alcoholysis reaction, comprising:
    placing the fat and/or oil of biological origin to be transesterified in a vessel; and
    adding methanol and a catalyst, the catalyst being a carbonic acid salt of 1-aminoguanidine and the alcoholysis being carried out at temperatures ranging from 50° C. to 120° C.

3. A method for the transesterification of fat and/or oil of biological origin by means of an alcoholysis reaction, comprising:
    placing the fat and/or oil of biological origin to be transesterified in a vessel; and
    adding methanol and a catalyst, the catalyst being 1-aminoguanidine hydrogencarbonate and the alcoholysis being carried out at temperatures ranging from 50° C. to 120° C.

4. The method according to claim 1, further comprising mixing another monohydric alcohol with methanol.

5. The method according to claim 4, wherein a mixture of methanol and ethanol is used.

6. The method according to claim 5, wherein the concentration of methanol is greater than 30 wt. %.

7. The method according to claim 1, wherein the alcoholysis is carried out at temperatures ranging from 65 to 80° C.

8. The method according to claim 1, wherein the reaction mixture refluxes during the reaction.

9. The method according to claim 1, wherein carbon dioxide is liberated in the reaction mixture and is entrained by the passage of an inert gas.

10. The method according to claim 1, wherein the proportion of free fatty acids in the starting fat is about 1 wt. %.

11. The method according to claim 1, wherein the proportion of free fatty acids in the starting fat does not exceed 0.2 wt. %.

12. The method according to claim 1, wherein the reaction mixture is stirred vigorously during the reaction.

13. The method according to claim 1, further comprising first separately dissolving the guanidine carbonate in methanol at elevated temperatures, with the elimination of carbonic acid to form free guanidine, and then mixing and reacting the free guanidine and methanol with the fat and/or oil to be transesterified.

14. The method according to claim 1, wherein the molar ratio of methanol to fat and/or oil is at least 2.3 to 1.

* * * * *